(12) United States Patent
Stetten

(10) Patent No.: US 6,599,247 B1
(45) Date of Patent: Jul. 29, 2003

(54) SYSTEM AND METHOD FOR LOCATION-MERGING OF REAL-TIME TOMOGRAPHIC SLICE IMAGES WITH HUMAN VISION

(75) Inventor: George DeWitt Stetten, Pittsburgh, PA (US)

(73) Assignee: University of Pittsburgh, Pittsburgh, PA (US)

(*) Notice: Subject to any disclaimer, the term of this patent is extended or adjusted under 35 U.S.C. 154(b) by 167 days.

(21) Appl. No.: 09/686,677

(22) Filed: Oct. 11, 2000

Related U.S. Application Data
(60) Provisional application No. 60/216,860, filed on Jul. 7, 2000.

(51) Int. Cl.⁷ ................ A61B 8/00; A61B 8/13
(52) U.S. Cl. ............ 600/443; 128/916; 600/437; 600/444
(58) Field of Search ........... 600/437, 443, 600/444, 445, 446, 449, 425; 73/618, 620, 625, 626, 627, 628, 629, 632, 633; 128/916

(56) References Cited

U.S. PATENT DOCUMENTS

| | | | |
|---|---|---|---|
| 4,058,001 A | * 11/1977 | Waxman | 600/443 |
| 4,200,885 A | 4/1980 | Hofstein | 348/163 |
| 4,381,787 A | * 5/1983 | Hottinger | 600/443 |
| 4,444,197 A | * 4/1984 | Koyano et al. | 600/443 |
| 4,509,524 A | * 4/1985 | Miwa | 600/443 |
| 4,624,143 A | * 11/1986 | Green | 600/443 |
| 4,862,892 A | * 9/1989 | Green | 600/443 |
| 5,224,481 A | * 7/1993 | Ishihara et al. | 600/443 |
| 5,230,338 A | 7/1993 | Allen et al. | 600/429 |
| 5,325,859 A | * 7/1994 | Ishihara et al. | 600/443 |
| 5,526,812 A | 6/1996 | Dumoulin et al. | 600/407 |
| 5,801,312 A | * 9/1998 | Lorraine et al. | 600/443 |
| 5,899,861 A | * 5/1999 | Friemel | 600/443 |
| 5,911,691 A | * 6/1999 | Mochizuki et al. | 600/443 |
| 6,210,331 B1 | * 4/2001 | Raz | 600/443 |
| 6,416,476 B1 | * 7/2002 | Ogasawara et al. | 600/443 |

FOREIGN PATENT DOCUMENTS

WO    WO 96/36897    11/1996

OTHER PUBLICATIONS

O'Toole R. et al., "Image Overlay for Surgical Enhancement and Telemedicine", Interactive Technology and the New Paradigm for Healthcare, Jan. 19, 1995, pp. 271–273.

Hill J, et al., "Telepresence Technology In Medicine: Principles and Applications", Proceedings of the IEEE, New York, US, vol. 86, No. 3, Mar. 1, 1998, pp. 569–580.

Masamune, et al., "*Three–Dimensional Slice Image Overlay System with Accurate Depth Perception for Surgery,*" Conference on Medical Image Computing and Computer–Assisted Intervention (MICCAI), 2000, Lecture Notes in Computer Science, Springer, Berlin, 1935:395–402.

(List continued on next page.)

*Primary Examiner*—George L. Walton
(74) *Attorney, Agent, or Firm*—Reed Smith LLP

(57) ABSTRACT

A device for combining tomographic images with human vision using a half-silvered mirror to merge the visual outer surface of an object (or a robotic mock effector) with a simultaneous reflection of a tomographic image from the interior of the object. The device maybe used with various types of image modalities including ultrasound, CT, and MRI. The image capture device and the display may or may not be fixed to the semi-transparent mirror. If not fixed, the imaging device may provide a compensation device that adjusts the reflection of the displayed ultrasound on the half-silvered mirror to account for any change in the image capture device orientation or location.

19 Claims, 7 Drawing Sheets

OTHER PUBLICATIONS

Masamune, et al., "Study on Three–Dimensional Surgical Support Display Using Enhanced Reality," Proc. Of 6th Annual Meeting of Japan Society of Computer Aided Surgery, Oct. 1997, pp. 113–114, Tokyo Denki University, Japan.

Nakajima, et al., "Surgical Navigation System with Intuitive Three–Dimensional Display," MICCAI 2000, pp. 403–411, Department of Orthopaedic Surgery, The University of Tokyo, Japan.

Mitschke, et al., "Interventions Under Video–Augmented X–ray Guidance: Application to Needle Placement," MICCAI 2000, pp. 858–868, Siemens AG Medical Engineering, Henkestr, Erlangen, Germany.

Blackwell, et al., "Augmented Reality and Its Future in Orthopaedics," Clinical Orthopaedic and Related Research, 1998, 354:111–122.

DiGioia, et al., "Computer–Aided Surgery," Cybersurgery, 1998, pp. 121–139, Wiley–Liss, Inc.

Fuchs, et al., "Towards Performing Ultrasound–Guided Needle Biopsies from within a Head–Mounted Display," Visualization in Biomedical Computing, 1996, pp. 591–600, Hamburg, Germany.

Fuchs, et al., "Augmented Reality Visualization for Laporoscopic Surgery," MICCAI, 1998, Springer, Berlin, 1996:934–943.

Azuma, R., "A Survey of Augmented Reality," A Survey of Augmented Reality in Presence: Teleoperators and Virtual Environments, 1997, 6(4):355–385.

Fry, et al., "Ultrasound–Guided Central Venous Access," Archives of Surgery, 1999, 134(7):738–741.

Holm, et al., "Interventional Ultrasound," Ultrasound Med. Biol. 1996, 22(7):773–789.

Cardinal, et al., "Interventional Procedures in Musculoskeletal Radiology—Interventional Techniques: Ultrasound–Guided Interventional Procedures in the Musculoskeletal System," Radiologic Clinics of North America, 1998, 36(3):597–604.

State, et al., Technologies for Augmented Reality Systems: Realizing Ultrasound–Guided Needle Biopsies, ACM SIGGRAPH, 1996, New Orleans, LA.

Sheafor, et al., "Abdominal Percutaneous Interventional Procedures: Comparison of CT and US Guidance," 1998, 207(3):705–710, Department of Radiology, Duke University Medical Center.

Fisher, et al., "Small Lymph Nodes of the Abdomen, Pelvis, and Retroperitoneum: Usefulness of Sonographically Guided Biopsy," Radiology, 1997, pp. 185–190.

Dodd, III, et al., "Sonography: The Undiscovered Jewel of Interventional Radiology," Radiographics, 1996, pp. 1271–1288.

Liu J., et al., "The Reliability of Ultrasound–Guided Core Needle Biopsy (US CNB) in the Evaluation of Non–Palpable Solid Breast Lesions," Laboratory Investigation, 1999.

Gupta, et al., "Sonographically Guided Fine Needle Aspiration Biopsy to Abdominal Lymph Nodes: Experience in 102 Patients," J. Ultrasound Med., 1999, 18(2):135–139.

Boland, et al., "Efficacy of Sonographically Guided Biopsy of Thyroid Masses and Cervical Lymph Nodes," AJR Am J. Roentgenol, 1993, 161(5):1053–1056.

Memel, et al., "Efficacy of Sonography as a Guidance Technique for Biopsy of Abdominal, Pelvic and Retroperitoneal Lymph Nodes," AJR Am. J. Roentgenol, 1996, 167(4):957–962.

* cited by examiner

SYSTEM AND METHOD FOR LOCATION-MERGING OF REAL-TIME TOMOGRAPHIC SLICE IMAGES WITH HUMAN VISION

RELATED APPLICATION DATA

This application claims the benefit of the earlier filing date of provisional application No. 60/216,860 filed Jul. 7, 2000.

FIELD OF THE INVENTION

The present invention generally relates to methods and devices for medical image displays and more particularly relates to methods and devices for combining a reflection of a tomographic image with human vision during subcutaneous medical procedures.

BACKGROUND OF THE INVENTION

Because human vision depends at least partially on the detection of reflected visible light, humans cannot "see" into objects through which light does not pass. In other words, humans cannot see into the interior sections of a non-transparent, solid object. Quite often, and in many different technology areas, this sight limitation may impede or hinder the effective completion of a particular task. Various partial solutions to this problem have been utilized in the past (miniature cameras, x-ray methodologies, etc.). However, there is a continued need for improvement to the methods by which the interior of an object is displayed, especially using a real-time imaging modality.

Perhaps in no other field is this sight limitation more of a hindrance than in the medical field. Clinical medicine often calls for invasive procedures that commence at the patient's skin and proceed inward to significant depths within the body. For example, biopsy needles introduced through the abdominal wall to take samples of liver tissue for diagnosis of cancer must pass through many centimeters of intervening tissue. One potential problem with such procedures is the lack of real-time visual feedback in the vicinity of critical structures such as the hepatic arteries.

Standard imaging modalities such as Computerized Tomography (CT) and Magnetic Resonance Imaging (MRI) can provide data for stereotactic registration of biopsy needles within targets in the liver, lungs, or elsewhere, but these methods are typically characterized by the physical displacement of the patient between the time of image acquisition and the invasive procedure. Real-time imaging modalities offer more immediate feedback. Among such real-time modalities, ultrasound may be well-suited for guidance of needles because it preferably is relatively portable, is inexpensive, produces no ionizing radiation, and displays a tomographical slice, as opposed to angiography, which displays a projection. Compared with angiography, ultrasound may offer the additional advantage that clinicians are not rushed through procedures by a desire to keep exposure times to a minimum.

Conventional two dimensional (2D) ultrasound is routinely used to guide liver biopsies, with the needle held in a "guide" attached to a transducer. The guide keeps the biopsy needle in the plane of the image while the tip of the needle is directed to targets within that same plane. This system typically requires a clinician to look away from his hands at a video monitor, resulting in a loss of direct hand-eye coordination. Although the clinician can learn this less direct form of coordination, the natural instinct and experience of seeing one's hands before one's eyes is preferred.

As a further disadvantage, the needle-guide system constrains the biopsy needle to lie in the image plane, whereas the clinician may prefer the needle to intersect the image plane during some invasive procedures. For example, when inserting an intravenous (IV) catheter into an artery, the optimal configuration may be to use the ultrasound image to visualize the artery in cross-section while inserting the needle roughly perpendicular to the image into the lumen of the artery. The prior art system just described may not be capable of accomplishing this task.

A related visualization technology has been developed where three dimensional (3D) graphical renderings of previously obtained CT data are merged with an observer's view of the patient using a partial or semi-transparent mirror, also known as a "half-silvered" mirror. A partial mirror is characterized by a surface that is capable of both reflecting some incident light as well as allowing some light to pass through the mirror. Through the use of a partial mirror (or other partially reflective surface) a viewer may see an object behind the partial mirror at the same time that the viewer sees the image of a second object reflected on the surface of the mirror. The partial mirror-based CT "Image Overlay" system requires independent determination of location for both patient and observer using external 6-degree-of-freedom tracking devices, so as to allow appropriate images to be rendered from pre-acquired CT data.

Another recently developed imaging technology merges ultrasound images and human vision by means of a Head-Mounted Display (HMD) worn by the human operator. The location and orientation of the HMD is continuously determined relative to an ultrasound transducer, using 6-degree-of-freedom tracking devices, and appropriate perspectives of the ultrasound images generated for the HMD using a graphics computer.

These prior art systems may not be appropriate for use with a practical real-time imaging device. Controlling the multiple degrees of freedom can be difficult, and the systems may have too many complex parts to be useful. As such, there is recognized a need in the art to provide a device capable of merging a human's normal vision of an object with an "internal" image of the object that emphasizes freedom of operator movement and/or simplicity of design.

SUMMARY OF THE INVENTION

The present invention contemplates, in at least one preferred embodiment, a device and method for merging human vision of the outside of a target object and a reflected tomographic image of the internal features of the same object. The invention may include an image capture device (e.g., a tomographic scanning device such as an ultrasound transducer), an image display device (e.g., a computer or video monitor), and a half-silvered mirror to "fuse" or superimpose the two images together.

In at least one preferred embodiment, the present invention provides a 2D ultrasound transducer, an image display, and a partially reflective, partially transparent, surface (e.g., half-silvered mirror) generally displaced between a target object and the image display. The transducer, the display, and the mirror may be fixedly attached to each other, or one or more elements may be partially or completely moveable with respect to the others. The movement may be accomplished through direct manipulation by the operator or with the use of one or more robotic arms.

In at least one preferred embodiment, the present invention provides a 3D ultrasound transducer, an image display, and a partially reflective surface broadly displaced between a target object and the image display. The image display may preferably display an appropriate slice of the 3D ultrasound data (effectively a 2D tomographic image) to enable a proper combined image to be seen when an observer looks at the target object through the partially reflective surface.

In at least one preferred embodiment, the present invention includes a series of gears, pulleys, or other motion transfer devices installed between the transducer, the display and the half-silvered mirror to allow the angle between the mirror and display to follow the angle between the transducer and the mirror as the transducer is moved. The present invention also contemplates various embodiments where the transducer is free to move in any direction or where robotic systems allow for the remote performance of procedures.

These and other details, objects, and advantages of the present invention will be more readily apparent from the following description of the presently preferred embodiments.

BRIEF DESCRIPTION OF THE DRAWINGS

The invention and its presently preferred embodiments will be better understood by reference to the detailed disclosure hereinafter and to the accompanying drawings, wherein.

DETAILED DESCRIPTION OF THE PREFERRED EMBODIMENTS

The invention contemplates, in at least one presently preferred embodiment, a method and device for merging or superimposing the reflection of a two dimensional tomographic image of the interior of a target object with the normal human vision view of the outside of that same target object. This methodology may be used in any application where viewing the interior of an object is desired, and the methodology is not limited to any particular industry or application. The interior image is preferably captured by any real-time imaging modality, where real-time does not necessarily indicate near-instantaneous display, but only that the target object has not moved significantly since the scanning was performed. One such real-time imaging modality is ultrasound.

Although this methodology and device can be used across many different fields of endeavor, the present invention may find particular applicability in the medical field. Because unwarranted or excessive intrusion into the interior portions of a human body may cause damage, infection, or other unwanted effects, these intrusions should be limited in both the number of instances and the scope of the intrusion. As such, it is preferable to perform subcutaneous procedures with at least some direct sighting of the interior of the patient. Because the medical device applications may be particularly useful, the present invention will be described with reference to such a medical device, but this exemplary disclosure should not limit the scope of this patent to any particular industry or use.

Figure 1:
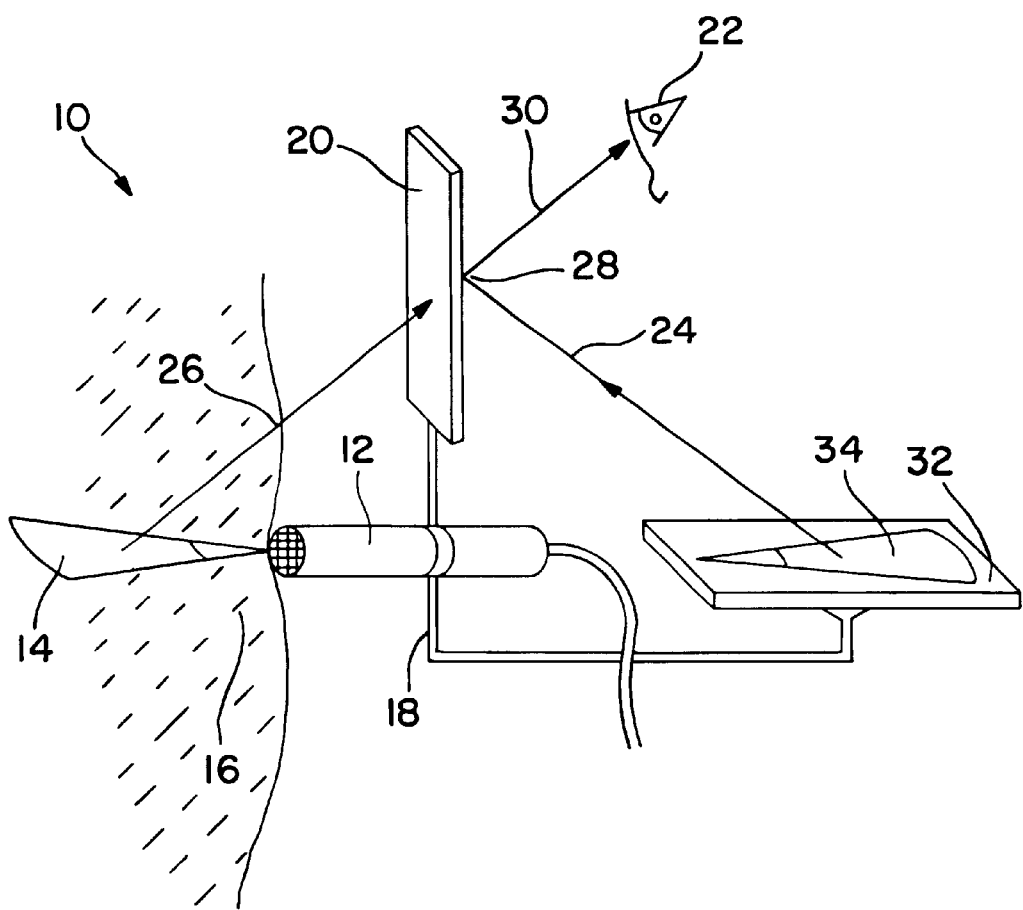
FIG. 1 is a schematic view of a device capable of merging a reflected tomographic image from a 2D ultrasound scanner with a direct view of a target image.

FIG. 1 shows an isometric view of a presently preferred embodiment of an imaging device 10 utilizing a two dimensional (2D) ultrasound transducer 12 capable of taking a B-Mode image slice 14 of a target object 16. In FIG. 1, there is a two dimensional ultrasound transducer 12 fixedly attached to a rigid frame 18. This transducer 12 is preferably a conventional ultrasound transducer that captures a "sonic" tomographic image slice 14 of the interior portion of the target object 16 (in this case a human patient).

Extending vertically from the middle region of the rigid frame 18 is a half-silvered mirror or other semi-transparent, semi-reflective, material 20. The half-silvered mirror 20 allows a user 22 (e.g., a doctor) to look through the mirror 20 at a target object 16 (e.g., a patient) located on the other side of the mirror 20 at the same time that a second image 24 is reflected on the front surface of the mirror (at 28). In this way, the direct target object image 26 and the reflected tomographic image 24 can be combined (image line 30) in the field of view of the user 22.

In FIG. 1, the half-silvered mirror 20 is depicted extending vertically up from the ultrasound transducer 12 midway along the transducer handle, but, in fact, the mirror 20 may be located at some other position in another vertical plane either behind or in front of the depicted vertical plane. More specifically, the FIG. 1 half-silvered mirror 20 could be translated forward or backward (or even tilted) as long as the display 32 is moved in a way that corresponds appropriately (as described in detail below).

At the opposite end of the rigid frame 18 from the transducer 12 is a flat panel display 32 showing the ultrasound image or other tomographic slice 34, with the image portion 34 facing upwards. This display 32 may be any low profile or flat display and may preferably be a liquid crystal display (LCD). When a user 22 looks at a target object 16 through the half-silvered mirror 20, the ultrasound display image 34 will be reflected along line 24 onto the front face of the half-silvered mirror (at 28). The user's sight line 30 will therefore be a combination or superimposition of the direct target object image 26 and the reflection of the ultrasound image 24.

In order to correctly visually merge the reflected ultrasound image 24 with the target object image 26, the ultrasound display image 34 may be reversed (along a horizontal plane), flipped (along a vertical plane), rotated, translated, and/or scaled (depending on the original image 34 location, orientation, and scale on the display 32) so that the reflected ultrasound image 24 on the face of the half-silvered mirror (at 28) correctly portrays the size, scale, and orientation of the ultrasound slice 14 being taken. In a practical sense, if one merely rotates the transducer 12 180 degrees, the ultrasound display image 34 will be flipped exactly as if this image manipulation was accomplished electronically.

A profile of a human operator's eye 22 is shown in FIG. 1 looking through the half-silvered mirror 20 at the target object 16 (patient). Because of well-known laws of light reflection, the ultrasound image 34 on the flat-panel display 32 will be reflected on the operator-side surface of the half-silvered mirror (at 28). Therefore, as the operator 22 looks at the target object 16 through the half-silvered mirror 20, the reflected ultrasound image 24 is merged (superimposed) with or onto the direct target object image 26. To the operator 22, these two images 24, 26 will effectively combine into one image 30 that includes the surface (normal vision 26) of the target object 16 and the interior (reflected ultrasound 24 or other tomographic reflection) of the target object 16. Because the angle of reflection of the ultrasound image follows the operator's sight angle as the operator's head moves, the merger 30 of these two images 24, 26 is independent of the location of the operator 22 (user). Therefore, the user 22 can move his head as well as take full advantage of stereoscopic vision to extrapolate the hidden parts of the invasive tool (e.g., needle) from the exposed parts of the same tool with respect to the anatomical structures in the ultrasound scan.

Because the direct target object image 26 and the reflected ultrasound image 24 are combined or superimposed on the surface of a half-silvered mirror (at 28) that may be naturally within the operator's direct line of sight (along 30), the operator 22 can preferably maintain direct hand-eye coordination throughout the procedure. This natural line-of-sight image combination 30 effectively allows the operator 22 to see "through" the surface (e.g., skin) of the target object 16 and into the underlying structures or layers of materials.

Further, although the present imaging device 10 may be used with virtually any imaging technology, using a nearly instantaneous imaging technology, such as ultrasound allows the interior and exterior views of the target object 16 to be nearly synchronous. However, the method may be applied to any real-time tomographic imaging modality, where "real-time" refers to any imaging modality that can update the displayed image 34 before the patient (target object 16) moves. As patient movement decreases, "slower" modalities become more useful. If a slower imaging technology is used (i.e., there is a substantial lag time between image capture and image display), the operator 22 may instruct the patient 16 to lie still so that the delayed interior image 34 will remain aligned with the current target object image 26. In this way, even a slower imaging technology may be used with the present invention.

Some possible "quick" imaging modalities include ultrasound, cine-CT and rapid MRI. Some "slower" modalities include conventional MRI, conventional CT, SPECT and PET. However, even these slow modalities may create an accurate combined image 30 so long as the target object 16 has not moved since the last image was captured. A needle or other intruding device may still be introduced using the overlaid image for guidance, provided the target object 16 has not moved. To increase the likelihood that the patient remains still, some combination of laser or ultrasonic range-finders, video cameras, and/or motion sensors (not shown) may be used to detect such movement and warn the operator 22 that the image will not be superimposed perfectly (at 28). Alternatively, these same sensor devices could detect exactly how far the target object 16 has moved since the last image capture and electronically correct the displayed image 34 and/or the location of the display 32 or mirror 20 (see below) to compensate for such target object movement.

Figure 2:
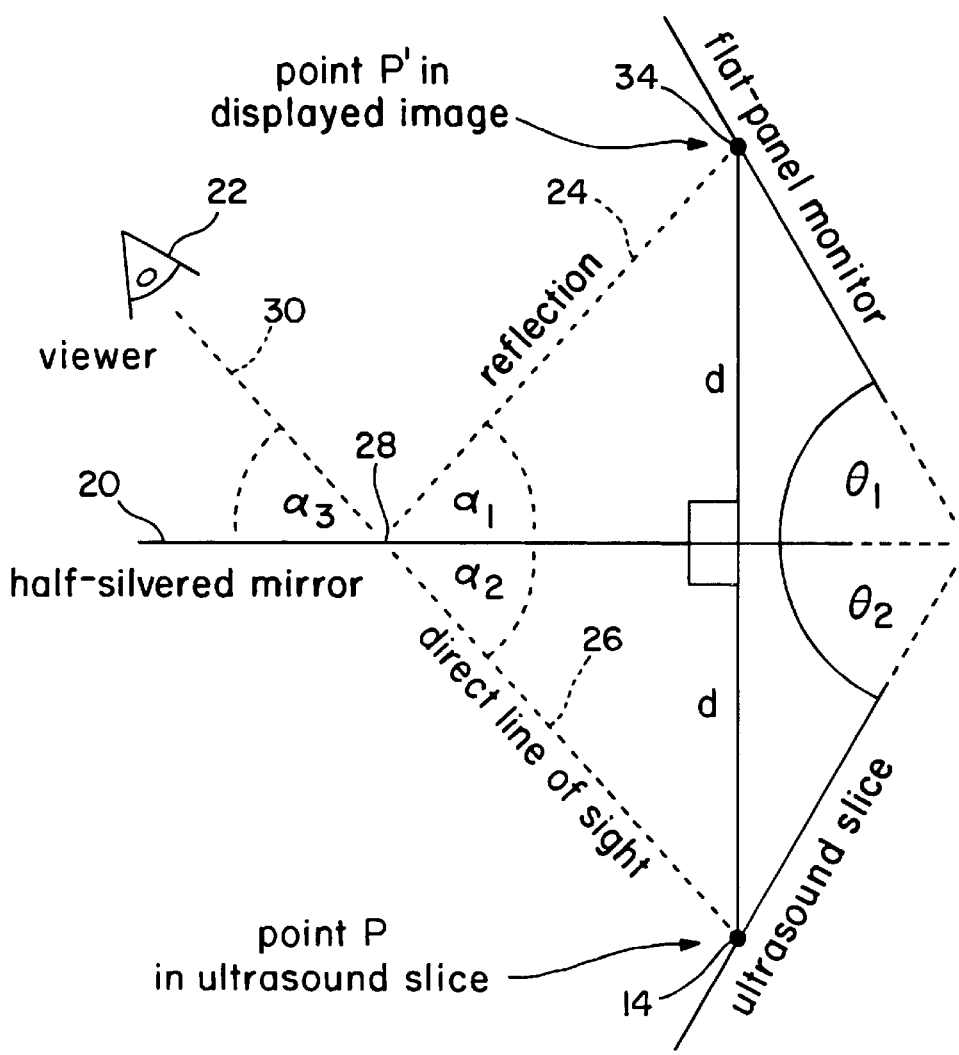
FIG. 2 is a schematic of the image angles that allow the operator to move in relation to the half-silvered mirror while maintaining image merger.
Figure 3:
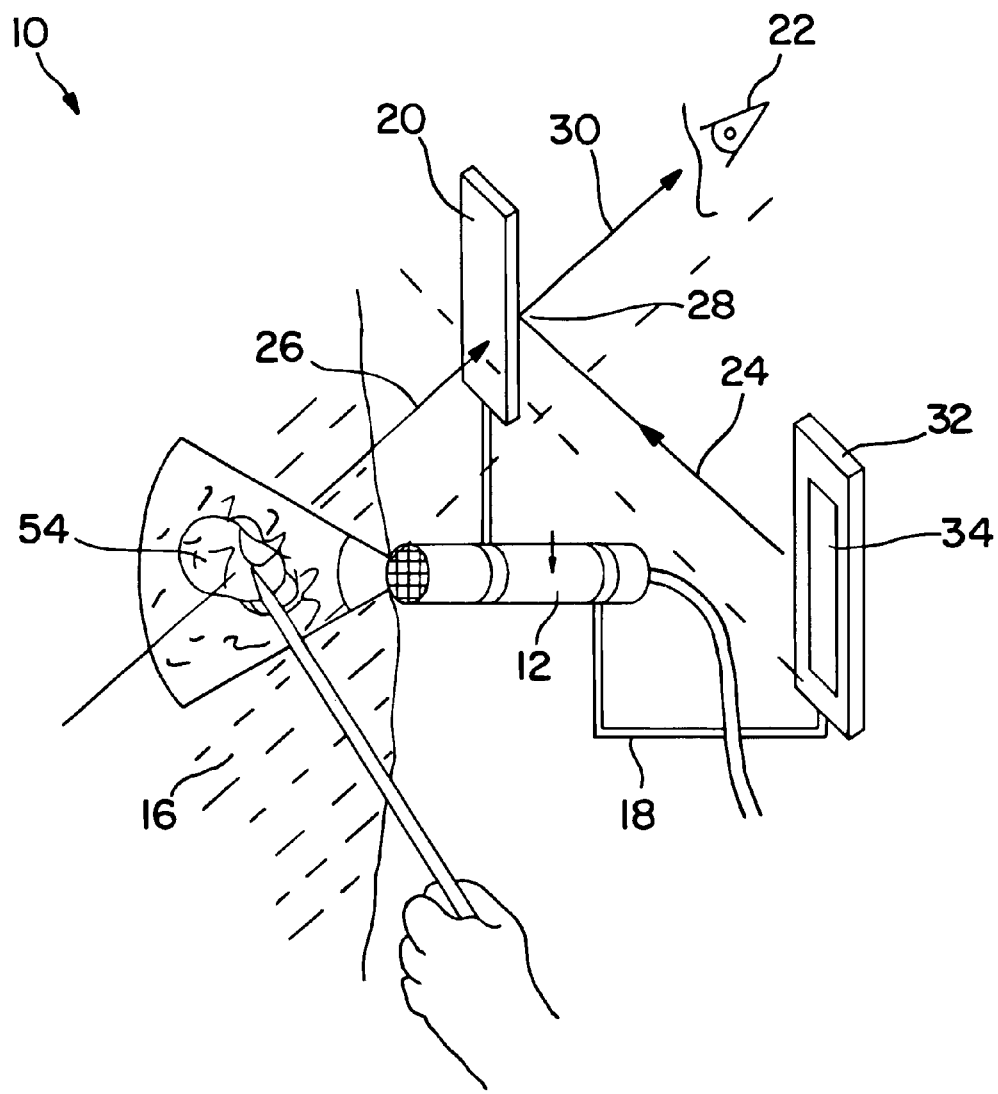
FIG. 3 is a schematic view of a device capable of merging a slice from a 3D scan with a direct view of a target image.

The mathematical requirements for locating the components of the apparatus are shown in FIG. 2. The half-silvered mirror 20 is preferably positioned between the tomographic slice 14 and its image 34 reflected on the flat-panel display, separated from each by the same angle $\theta$ ($\theta_1 = \theta_2 = \theta$). In essence, the half-silvered mirror 20 bisects the angle $2\theta$. As seen in FIG. 3 (below), $\theta$ can approach zero. Because the mirror 20 in FIG. 2 bisects the angle $2\theta$, point P in the ultrasound slice 14 and its corresponding image P' in the flat panel display 34 are both distance d from the half-silvered mirror 20. The line between the point P in the slice 14 and its image P' in the display 34, along which d is measured, is orthogonal to the plane of the semi-transparent mirror 20.

The figure shows the eye of the viewer 22, to whom the ultrasound display will be superimposed (along 30) on the corresponding physical location of the slice irrespective of the viewer's location. The angle of incidence from the flat panel display 34 to the face of the half-silvered mirror (at 28) is labeled $\alpha_1$ in FIG. 2. By well-known laws of light reflection, the angle of reflection $\alpha_3$ is equal to the angle of incidence $\alpha_1$. Because the mirror 20 bisects $2\theta$ and further by well-known laws of geometry, the "incidence" angle $\alpha_3$ from the corresponding point 14 in the target object 16 to the back of the half-silvered mirror 20 is also equal ($\alpha_1 = \alpha_2 = \alpha_3 = \alpha$). In this way, regardless of viewer position, the direct target object image 26 and the reflected tomographic slice image 24 will always coincide to combine image 30.

FIG. 3 shows a presently preferred embodiment of the imaging device 10 utilizing a three dimensional (3D) ultrasound transducer 12. As with the 2D transducer described above, the FIG. 3 embodiment details a half-silvered or partial mirror 20 fixedly attached to the transducer 12 and extending vertically upwards therefrom. In this embodiment, the transducer 12 is capable of capturing 3D imaging data of a scanned volume 54 (e.g., a Real Time 3D (RT3D) ultrasound image). The image 34 that is shown on the flat-panel display 32 (and therefore reflected 24 onto the partial mirror 20) is preferably a 2D tomographic slice through the scanned volume 54 in the target object 16 (for example, a "C-Mode" slice, parallel to the face of the transducer 12). This 2D tomographic image 34 may be mathematically computed from the collected 3D imaging data by a computer (not shown). The flat-panel display 32 should be properly located and oriented to precisely reflect 24 onto the half-silvered mirror (at 28) the location of the corresponding tomographic image within the target object 16. Once again, the image 34 on the display 32 is preferably electronically translated, rotated, scaled and/or flipped to complete proper registration independent of viewer location, as necessary.

Compared to the "Image Overlay" CT-based system using previously obtained data or any other "lagging" imaging scheme, ultrasound or other "real-time" data is preferred so that the present location of the patient (target object) 16 need not be independently established or registered by the imaging device. Whatever is currently in front of the transducer will simply appear superimposed on the operator's visual field at the appropriate location. Furthermore, the present invention preferably displays only a single slice, as opposed to a complete 3D rendering as in the "image overlay" CT system (described above). Therefore, the visual image merger 30 can be made independent of the observer's location simply by placing the ultrasound display 32 where its reflection 24 in the half-silvered mirror 20 superimposes on the direct view 26 of the target object 16. Since the displayed tomographic image 34 is 2D and is reflected precisely on its proper location in the target object 16, the correct combination 30 of these views 24, 26 is independent of viewer 22 location. This may be simpler and more efficient than superimposing 3D renderings.

The devices and methods as described above include rigidly attaching a semi-transparent mirror 20 and flat-panel display 32 to the tomographic scanning device 12 (or other image capture device). This rigid fixation and the associated bulk of the complete device 10 may reduce the ability of the operator 22 to manipulate the scanning device or transducer 12 during a procedure. There are several ways in which the freedom and ability of an operator 22 to manipulate the image capture device 12 may be increased.

For example, a linkage system of levers, weights, pulleys, and/or springs (not shown) could be constructed, while maintaining the rigid relationship between the device components (scanner 12, mirror 20, display 32), to aid in the manipulation of the entire apparatus 10. This linkage system of levers, weights, pulleys, and/or springs may cantilever or otherwise reduce the amount of force necessary to manipulate the apparatus 10. A similar configuration, for example, is often used in hospitals to aid in the manipulation of heavy lights during surgery. These levers, weights, pulleys, and/or springs are preferably attached to the ceiling or to a floor stand.

Alternatively, the operator 22 may obtain greater flexibility to manipulate the transducer 12 through a system of gears and/or actuators that keep the angle ($\theta_1$) between the display 32 and the half-silvered mirror 20 equal to the angle ($\theta_2$) between the transducer 12 and the mirror 20. As the user 22 moves the transducer 12 in various ways, additional gears, actuators, and/or encoders of linear and/or angular motion could accommodate this transducer motion (and corresponding change in $\theta_2$) by providing equivalent motion of the displayed ultrasound image 34 (and corresponding change in $\theta_1$) through physical manipulation of the display screen 32 and/or electronic manipulation of the image 34 displayed on the screen 32. These gears, actuators, and/or image manipulations preferably keep the appropriate angle ($\theta$) and location between the display 32 and the half-silvered mirror 20 so that the user 22 can move the transducer 12 and still see a proper combination image 30 of the target object image 26 and the reflected ultrasound image 24 independent of viewer location. Such a system could be made to accommodate 6 degrees of freedom for the transducer, including 3 rotations and 3 translations. As with the above embodiments, this embodiment preferably entails physical attachment of the transducer 12 to the rest of the apparatus (which may hinder use of the device 10).

Figure 4:
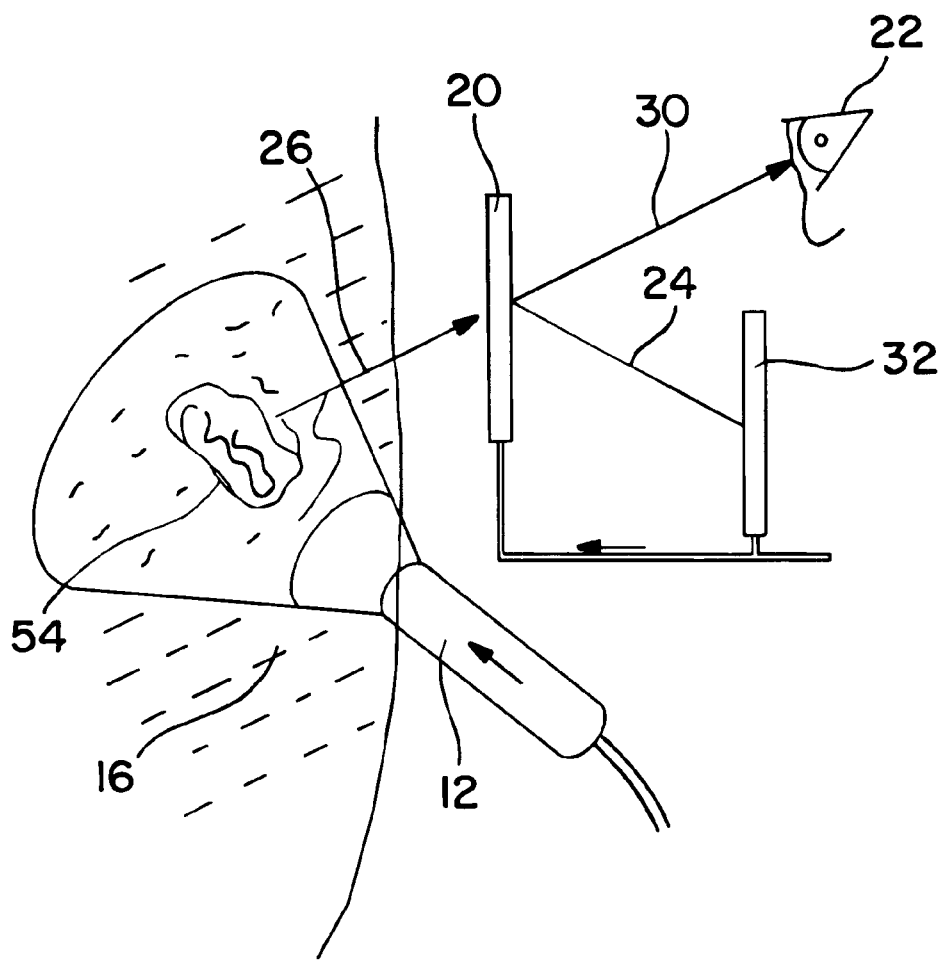
FIG. 4 is a schematic view of an imaging system with the image capture device removed from the remainder of the system.

To further increase the ability of the operator 22 to manipulate the transducer 12 (or other tomographic scanning device), the transducer 12 (or other image acquisition device) may be physically freed from the rest of the apparatus. By continuously determining the relative angles and location of the transducer 12 with respect to the half-silvered mirror 20 using a system such as the commercially available "FLOCK-OF-BIRDS" or "OPTITRACKER" systems, the angle ($\theta_1$) and orientation of the display 32 with respect to the mirror 20 could likewise be adjusted to compensate for this transducer manipulation. One embodiment of a system for freeing a 3D ultrasound transducer 12 is shown in FIG. 4. The appropriate slice through the 3D ultrasound data 54 is computed and displayed (on display 32) so as to effect a merger 30 of the two images 24, 26 on the face of the mirror 20.

Similarly, for 2D ultrasound, the manipulability of the transducer 12 may be especially important when searching for a target. The problem can preferably be addressed by detaching the transducer 12 from the rest of the assembly (the mirror 20 and the flat-panel display 32). A 6-degree of freedom tracking device such as the "FLOCK-OF-BIRDS" or "OPTITRACKING" system may be attached to the handle of the transducer 12. The flat-panel display 32 may be detached from the mirror 20 and controlled by a series of motors such that the display 32 would be made to remain exactly in the reflected plane of the ultrasound slice, as determined by the tracking system on the transducer handle. Such display movement will preferably occur according to well-known principles of robotics.

Such a motorized device may lag behind the movement of the transducer 12 during rapid manipulations of the transducer 12 by the operator 22, but would preferably catch up with the operator at relatively motionless periods when the operator 22 had located a desired target. The mirror 20 may preferably be held motionless relative to the target object 16, establishing the frame of reference for both the transducer tracking system and the motorized display 32. Alternatively, the mirror 20 may be motorized and the display 32 held constant (or both the mirror and the display could move).

The other degrees of freedom which may be necessary to visually fuse 30 (superimpose) the displayed ultrasound image 24 with the actual target image 26 may be supplied by graphical manipulation of the displayed image 34 on the flat-panel display 32, based on the tracking of the transducer 12. As with the fixed and geared assemblies described above, the motorized display 32 and graphical manipulation of the displayed image 34 preferably provides visual "fusion" 30 of the reflected ultrasound image 24 with the actual target object image 26 independent of operator 22 or target object 16 location.

In one presently preferred embodiment of the invention, two robotic arms, or a single paired robotic device, manipulate both the transducer 12 and the display 32 (and/or the mirror 20) under remote control in such a way that the visual fusion 30 is maintained. This may eliminate the need to track the transducer 12, replacing it with feed-forward remote control of the transducer location via a joystick or other controller. The simultaneous control of two robotic devices whose motions may be as simply related as being mirror images of each other, may be accomplished in a fairly straightforward manner, and may exhibit a more synchronous image fusion.

A natural pivot-point for the display monitor may be the reflection of the point of contact between the transducer and the target object because, during many procedures, the operator tends to rotate the ultrasound transducer in all three rotational degrees of freedom around this point (to find a desired target). Thus, for the simultaneous control of two robotic devices just described, rotating the display monitor with three degrees of freedom around this point may be preferred. For systems that move the display while tracking a manually manipulated transducer, at least one translational degree of freedom may be needed to allow the display monitor to become coplanar with the ultrasound slice.

Calibration of the fixed system and development of the servo-linked (motorized) display system or the dual robotic system just described may require careful consideration of the degrees of freedom in the registration process. First, consider only the geometric transformation, i.e., assume the scale of the captured slice and the displayed image are identical and undistorted. To complete the geometric transform registering the reflection of the ultrasound image to the actual slice, we need to satisfy 6 degrees of freedom. First we have 3 degrees of freedom to manipulate the display physically into the plane of the slice reflection. This can take the form of two rotations to make the display screen reflection parallel to the slice and one translation orthogonal to the display screen to bring it into precisely the same plane.

Once the display reflection and the slice are in the same plane, we need 3 more degrees of freedom to match the image and the slice, which may be achieved through two translations and one rotation of the image on the display. In essence, the 6 degrees of freedom place the display in the proper physical plane to reflect the image on the half-silvered mirror (3 degrees of freedom) and then rotate and translate the image on the display so that the correctly placed reflection is properly aligned (3 additional degrees of freedom) on the mirror with the actual target object image.

Beyond the geometric transformation, further calibration may be required. First, the proper scale must be calibrated. This includes isotropic scale (similarity transform) and non-isotropic scale (affine transform). Further corrections may be required for non-linear geometry in both the imaging system and the display by warping of the image.

To the extent that the geometric properties of the slice do not change with tissue type, and the slice geometry does not change as the transducer is moved relative to the target object, calibration of the system 10 may only need to be performed initially, using a phantom target object (not an actual patient). Such calibration will suffice for slice geometry due only to the scanner. Further changes in image geometry due to tissue properties will depend on transducer location relative to the tissue. These changes may be due to differences in the speed of sound in different tissue types. It may be possible to correct for these using image analysis techniques as known and developed in the art.

A problem with calibration may arise because a phantom in a water tank that is easily scanned using ultrasound will appear displaced to human vision due to refraction at the air-water interface. Several solutions are described here to this problem. One solution may use a rod that intersects both the reflected image (in air) and an ultrasound slice displaced along the rod (water). The display may then be physically moved or rotated, and the image on the display may be electronically moved or rotated, to make the rod appear to intersect the corresponding reflected ultrasound image appropriately.

A second calibration solution includes the use of a calibration phantom. The phantom is placed in water or some other ultrasound transmitting (but light refracting) medium and scanned by the image capture device. The image is "frozen" (still picture) on the display and reflected off of the half-silvered mirror. Without moving the calibration phantom, the water or other medium is drained or removed from the calibration setup. The user can then adjust the display or the image on the display until the "frozen" reflected scan image of the phantom aligns with the direct sight image of the calibration phantom. Many other calibration schemes could be used within the scope of the present invention.

Figure 5:
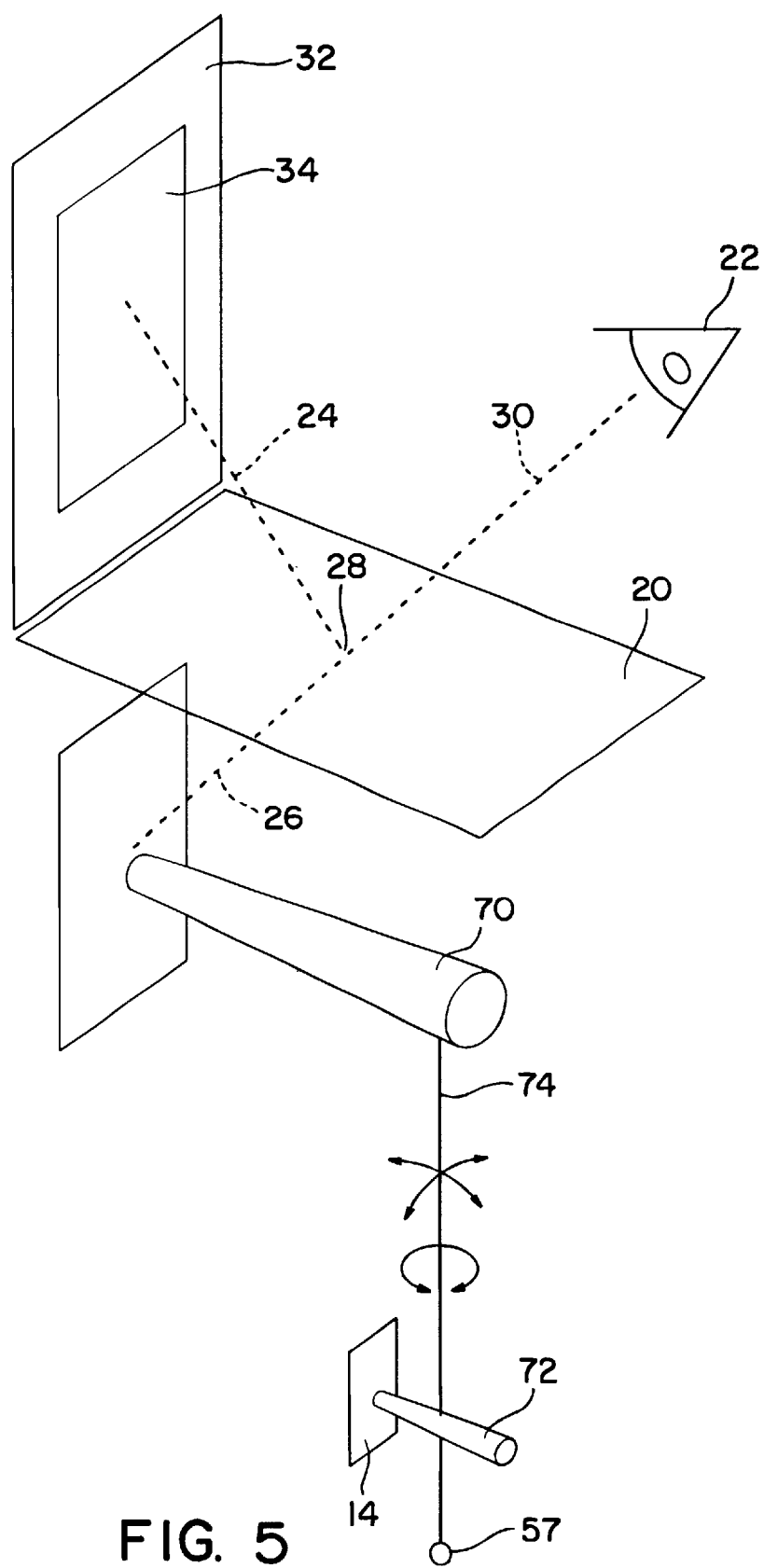
FIG. 5 shows the methodology applied to remote operation using a mock effector in the field of view.
Figure 6:
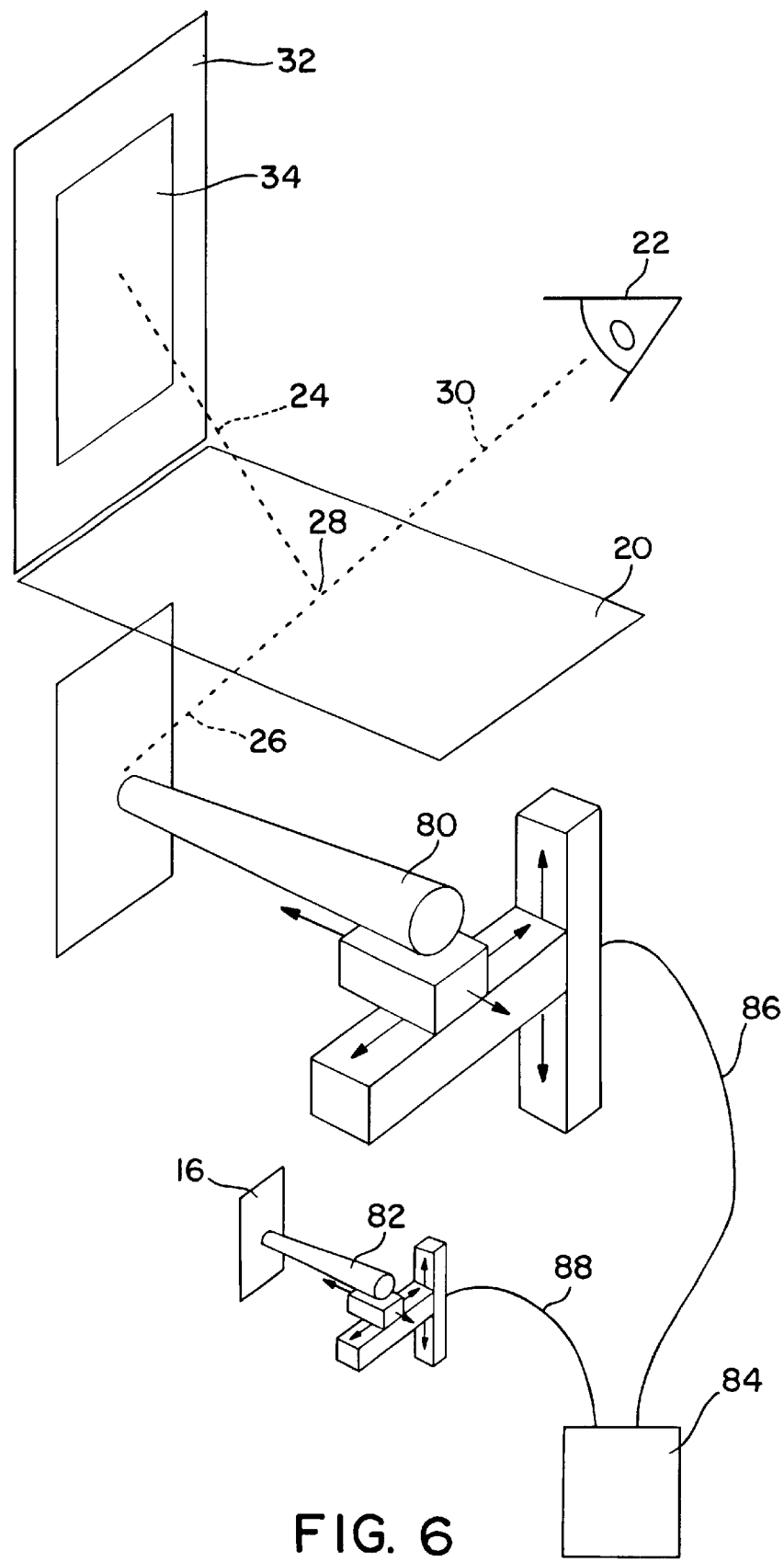
FIG. 6 shows the methodology applied to remote operation utilizing a remote-controlled effector.

In one presently preferred embodiment of the present invention, a "remote" procedure is performed through the use of a tomographic scanning device and surgical implements controlled remotely with a mechanical or robotic "mock effector" in the operator's field of view instead of the actual target object being in the operator's field of view. A mock effector is a physical replica of the actual invasive instrument, preferably of identical shape but not necessarily identical scale. The mock effector may either be directly controlled by the operator (FIG. 5) with mechanical linkages, encoders and/or tracking devices relaying the desired motion to the actual effector, or alternatively the operator may use a remote control to activate both the mock effector and actual (surgical) effector with corresponding motions (FIG. 6).

For example, a procedure may involve using a hypodermic needle or micro-pippette to take samples in a certain plane. In FIG. 5, the tomographic scanning device (not shown) may be aligned to capture a slice 14 of the target object from which the sample may be taken. The action of the actual surgical needle 70 may be controlled remotely by operator 22 manipulation of a mock effector (needle) 70 in the user's field of view demonstrating the precise motion of the actual remote effector 72, although possibly at a different scale. The scale (as well as the location and orientation) of the mock effector 70 would match that of the reflected tomographic image 24 (to make the combined image 30 an accurate representation).

In this example, a mock needle 70 may be present in front of the operator 22 (remote from the target object). The operator 22 preferably looks through the half-silvered mirror 20 at the end of the mock effector 70. The operator's field of vision is a merged image 30 of the direct view 26 of the mock effector and the reflection of the tomographic slice 24. If the actual needle 72 performing the procedure on the patient (target object 16, not shown, through which tomographic slice 14 is acquired) is of a different scale than the mock effector needle 70, then the tomographic image 34 displayed on the monitor 32 is preferably moved and/or scaled so that the reflected tomographic image 24 and the direct view 26 of the mock effector are of equal size, scaling, and orientation at the surface 28 of the half-silvered mirror 20.

The mock effector needle 70 and the actual surgical effector needle 72 are preferably connected through some sort of control mechanism 74. In FIG. 5, this control mechanism is shown as a direct mechanical link 74, being a rod fixed at one end by a ball-and-socket 57 to allow 3 degrees of rotation. As the operator manipulates the mock effector 70, the actual effector 72 will move correspondingly (although on a smaller scale). Similarly, the control mechanism may be some type of tracking or encoder device that registers the movement of the mock effector 70 and transfers this movement to the actual surgical effector 72. In this way, the operator can manipulate a mock effector 70 and cause a procedure to be performed on a target object at a remote location.

This remote procedure model may be useful for extremely small scale procedures. For example, assume a microscopic region of a patient must be cut (e.g., a cancer cell removed or a cornea operated upon). In the region of a very small cutting implement, a specialized tomographic scanning modality (such as Optical Coherence Tomography (OCT) or a high frequency (100 MHz) ultrasound) may be used to capture an image slice. At a remote location, a doctor may preferably look through a partial mirror with a reflection of the tomographic slice on its face superimposed upon a mock cutting implement whose motion is linked to that of the actual cutting implement. Although the actual procedure occurs on a microscopic scale, both the tomographic slice and the mock effector can be magnified or scaled up to a point that allows the doctor to perform the procedure in a more relaxed and accurate manner. As long as the mock effector is scaled up to a similar size as the tomographic slice, the overlay of the images may be accurately located and oriented with respect to each other. In this way, small scale medical (or non-medical) procedures may be easier to perform. Similarly, large scale procedures such as undersea robotics using sonar-based tomographic imaging may be performed remotely at a smaller scale than they actually occur.

FIG. 6 details one possible robotic version of the present invention. The FIG. 6 remote application is generally similar to the FIG. 5 implementation with the addition of a control box 84 used to control the motion of both the mock effector 80 and the actual surgical effector 82. As in the previous example, the operator 22 looks through the surface of the half-silvered mirror 20 at the working end of a mock effector 80. A tomographic image 34 of the target object 16 is displayed on a monitor 32 and reflected along line 24 onto the surface of the half-silvered mirror 28. The operator's filed of view includes the merger 30 of these two images 24, 26.

In this example, however, the operator 22 preferably does not directly manipulate the mock effector 80. Instead, some type of control, for example a joystick, keyboard, voice activated software, or other device, is manipulated by the operator 22. This control device causes the movement of both the mock effector 80 (through control line 86) and actual effector 82 (through control line 88). In FIG. 6, each of these effectors 80, 82 can be moved with 3 degree of freedom movement. The mock effector 80 can again be scaled larger or smaller to make the manipulation of the actual effector 82 more convenient. Preferably the size, scale, and orientation of the tomographic image 34 displayed on the monitor 34 is matched to the size, shape, and orientation of the mock effector 80.

For robotic versions of the present invention, the effector 82 that interacts with the patient 16 need not necessarily be a mechanical surgical tool. For example, the effector could be a laser, RF (radio frequency) transmitter, or other device for delivering or imparting energy or matter on a target object. In these cases, the mock effector used by the operator may include some kind of demonstration of the energy or matter delivered, either expected or measured, to the patient. For example, an isosurface of expected RF field strength may be physically constructed and mounted on the mock effector used by the operator such that the field model intersects the reflected image appropriately. In this way, the operator can take into account the field of the effector's use, as well as the effector itself.

The present invention may also depend on the lighting used on or around the device. For example, light that hits the surface of the half-silvered or partial mirror from above (operator-side) may introduce unwanted reflections in the semi-transparent mirror. In this case, the target object will be more difficult to see. Alternatively, light that comes from a source beneath the half-silvered mirror (on the same side of the mirror as the target object) may increase the clarity of the target object image without introducing unwanted light reflections onto the half-silvered mirror. Various types of lighting (visible, ultraviolet) as well as paints, markings, and light emitting markers on the targets or tools themselves may have different properties that are adjustable to change the contrast, intensity, and interpretability of the image superimposition.

Alternative forms of light may also be used to register locations in the ultrasound during a procedure. These alternative light sources can be used to identify certain features of the target object in addition to the 3D visual cues inherent to superimposition of the reflected image. For example, a plane of laser light can be created with a movable mirror and a laser such that any real object (part of target object or mock effector) that intersects the plane of laser light will be "marked" by the colored lines of the laser light. Such a laser marking system could be used with a computer vision system to permit automated detection and location determination of the intersection point of the located object and the light plane. This system may be used for automated calibration with corresponding features detected in the tomographic image.

Light sources could also be arranged relative to opaque shields so that only certain parts of the target object are illuminated, such as all parts beyond the reflected tomographic image. Thus the image would fall on what would effectively be a clipping plane through the object, with all parts of the image closer to the viewer not illuminated. Sound, tactile, and/or other forms of feedback may be provided to the operator based on the location of tools relative to the reflected image. These feedback indicators may alert the operator when contact is made, for example between the tip of a needle and the reflected slice.

Various techniques may be used to alter the image as viewed on the low-profile display. The image may be rotated, translated, scaled, or distorted, as previously described, or otherwise cropped or manipulated in many ways according to the needs of the user of the system. For example: extraneous parts of the image may be removed; specific anatomical targets may be automatically identified and graphically enhanced; surgical tools may be tracked and their hidden sections graphically simulated; and/or other useful information may be superimposed on the displayed image for the operator relating to the invasive procedure.

In all, the present invention may be useful for many medical procedures including amniocentesis; many forms of surgery; soft tissue biopsy of organs such as liver, kidney, or breast; and procedures such as the insertion of central venous lines, or even peripheral intravenous catheters. In brain surgery, for example, deformation of the brain after removal of portions of the skull leads to inaccuracy of registration in non real-time modalities such as conventional CT. Real-time guidance using ultrasound may compensate for such deformations, as well as provide adaptive guidance during the removal of an abscess, for example, or in other cases where structures may change shape or location during procedures. Another example is monitoring and correction of tissue infiltration during the infusion of cancer drugs into large veins. The invention may positively effect the success and flexibility of these and other invasive procedures.

Since the visual image merger is independent of viewer location, two or more human operators may work together in the same field of view, assisting each other manually and/or offering consultation. The invention may be valuable in teaching, for example, by clarifying the content of ultrasound images through its location in the target object.

As briefly mentioned above, the version of the device using a mock effector could be used at microscopic scales, for example, to insert micro-pippettes into individual cells under OCT guidance to gather intracellular samples to determine whether the cells are of a cancerous nature (or to delivery therapy to a single cell). Other possible examples include the use of very high frequency ultrasound to guide microscopic surgery on the cornea, and high resolution MRI to guide biopsies of tissue samples of small animals. It may also be used to guide the administration of radiation and other non-invasive procedures, or the present invention may be used in many other technical and non-technical applications.

One or more of the above embodiments may be oriented toward a portable version of the present invention. The size, shape, and materials used may be minimized so that the entire apparatus can be carried by a single user (or a few users) to the site of a procedure. An ultrasound transducer is preferably used in the portable embodiment because of its small size and ease of use. These embodiments may be especially suited for use in the battlefield for the removal of foreign bodies such as bullets or shrapnel.

Figure 7:
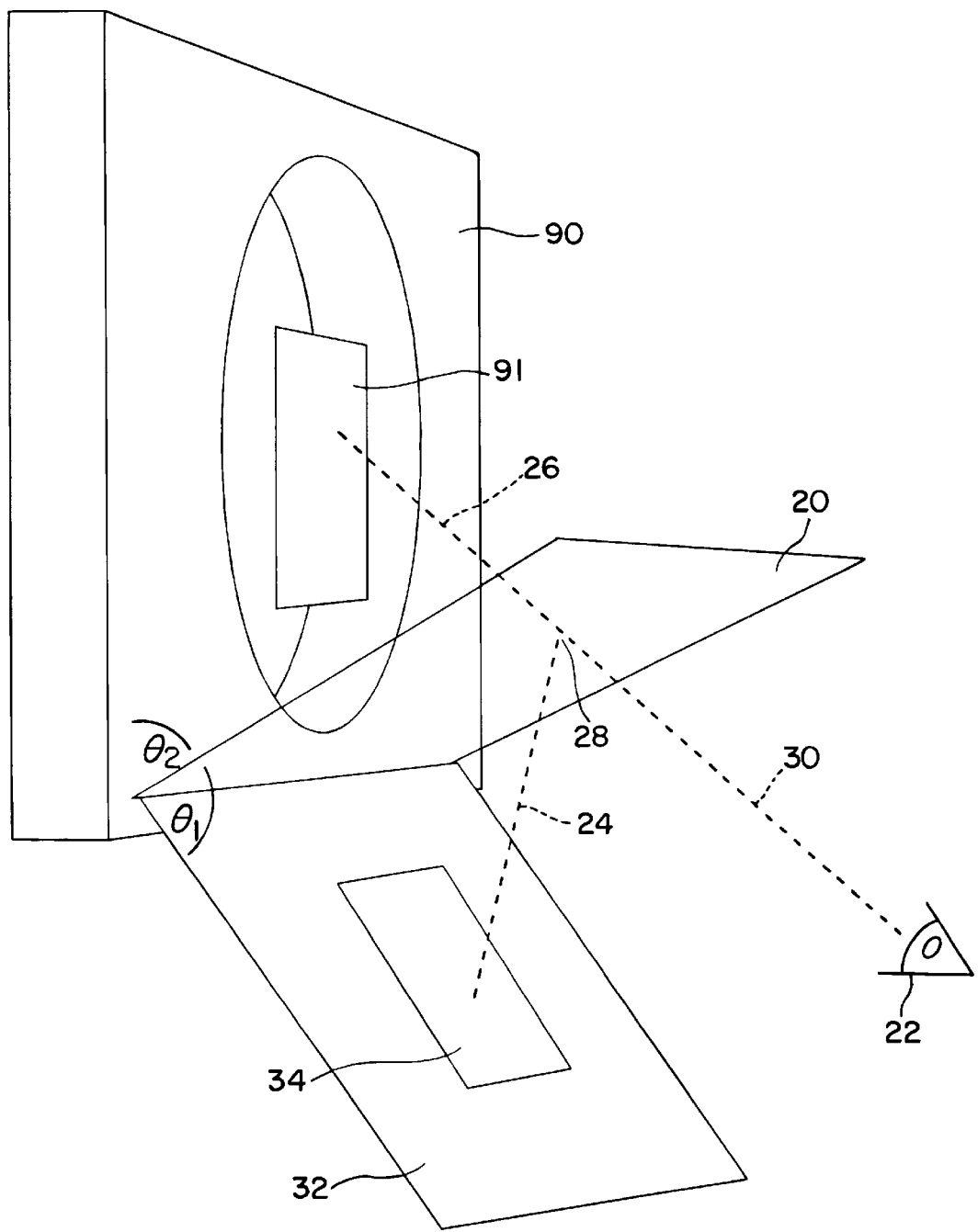
FIG. 7 is a schematic diagram of the present methodology applied to the front of a large imaging machine such as a CT scanner.

The ultrasound transducer in the above portable version may be replaced (towards the opposite end of the size spectrum) with a comparatively massive CT or MRI scanner (see, FIG. 7). The principle of operation is still based on a controlled geometric relationship between the scanner, the mirror 20, and the display 32, just as in the above embodiments. In essence, the angle ($\theta_1$) between the display 32 and the half-silvered mirror 20 should be equal to the angle ($\theta_2$) between the mirror 20 and the slice 91 through the target object within the gantry of the CT or MRI scanner 90.

The image from a CT or MRI machine can often be converted into an appropriate tomographic slice within less than one minute from the image scanning. Once a CT scanner is no longer transmitting X-rays (after the image is captured), there will be no harmful exposure to the operator. As seen in FIG. 7, the gantry 90 of these machines may provide ample access for a doctor or other user 22 to perform an invasive procedure on a patient within the CT machine. Furthermore, if the space in the gantry 90 is not sufficient for a particular procedure, the patient (or other target object) may be moved out of the machine a known distance, and the image 34 of the tomographic scan may then be shifted by that same amount (provided the patient did not move in any other way).

The above specification describes several different embodiments and features of a device and method for fusing or superimposing a direct object image and a reflected image into a combined image that includes both a subsurface tomographic image of a target object and a visual surface image of either the same object or a mock effector. Various parts, selections, and/or alternatives from the various embodiments may preferably be interchanged with other parts of different embodiments. Although the invention has been described above in terms of particular embodiments, one of ordinary skill in the art, in light of the teachings herein, can generate additional embodiments and modifications without departing from the spirit of, or exceeding the scope of, the claimed invention. Accordingly, it is to be understood that the drawings and the descriptions herein are proffered by way of example only to facilitate comprehension of the invention and should not be construed to limit the scope thereof.

What is claimed is:

1. An imaging device comprised of:
   an image capture device for capturing an image of the internal structure of a target object;
   a display for displaying a captured image from the image capture device; and
   a partially reflective surface oriented to reflect the captured image to an operator of the imaging device such that the reflected captured image is merged with a direct view of the target object independent of the viewing location of the operator.

2. The imaging device of claim 1, wherein said image capture device captures a two dimensional image.

3. The imaging device of claim 2, wherein said two dimensional image is an ultrasound image.

4. The imaging device of claim 1, wherein said image capture device captures a three dimensional data set.

5. The imaging device of claim 4, wherein said image capture device captures a three dimensional ultrasound image.

6. The imaging device of claim 1, wherein said image capture device, said display, and said partially reflective surface are fixedly attached to each other.

7. The imaging device of claim 6, further including a linkage system that enables manipulation of the imaging device.

8. The imaging device of claim 1, further including a laser marking system.

9. The imaging device of claim 1, wherein said image capture device is rotatably attached to the partially reflective surface.

10. The imaging device of claim 1, wherein said image capture device is mechanically separated from the partially reflective surface.

11. The imaging device of claim 1, wherein said image capture device is directly manipulated by the operator.

12. The imaging device of claim 1, further including at least one robotic arm capable of manipulating the image capture device.

13. A method for viewing a target object, comprising the steps of:
   capturing a tomographic image of the target object;
   displaying said tomographic image;
   reflecting said displayed tomographic image onto a half-silvered mirror such that an operator can directly view the target object through said half-silvered mirror merged with the tomographic image reflected onto the half-silvered mirror, wherein said merger is independent of operator viewing location.

14. The method of claim 13, wherein said tomographic image reflected onto the half-silvered mirror is updated in real-time.

15. The method of claim 13, further including the step of activating a mock effector to control an actual effector remote from said mock effector, wherein said actual effector performs a procedure remote from the operator of the mock effector.

16. The method of claim 15, wherein said mock effector and said displayed tomographic image are scaled up to a size that is larger than the actual effector and the target object respectively.

17. The method of claim 15, wherein said mock effector and said displayed tomographic image are scaled down to a size that is smaller than the actual effector and the target object respectively.

18. The method of claim 15, wherein said operator directly controls said mock effector.

19. The method of claim 15, wherein said operator uses a remote control mechanism to control both the mock effector and the actual effector.

* * * * *